United States Patent
Du et al.

(10) Patent No.: US 9,921,194 B2
(45) Date of Patent: Mar. 20, 2018

(54) WAVY MICRO GAS CHROMATOGRAPHY COLUMN

(71) Applicant: University of Electronic Science and Technology of China, Chengdu, Sichuan (CN)

(72) Inventors: Xiaosong Du, Sichuan (CN); Huan Yuan, Sichuan (CN); Xulan Zhao, Sichuan (CN); Penglin Wu, Sichuan (CN); Yadong Jiang, Sichuan (CN)

(73) Assignee: University of Electronic Science and Technology of China, Chengdu, Sichuan (CN)

( * ) Notice: Subject to any disclaimer, the term of this patent is extended or adjusted under 35 U.S.C. 154(b) by 72 days.

(21) Appl. No.: 15/164,841

(22) Filed: May 25, 2016

(65) Prior Publication Data

US 2016/0266073 A1    Sep. 15, 2016

(30) Foreign Application Priority Data

Sep. 11, 2015    (CN) .......................... 2015 1 0577996

(51) Int. Cl.
*G01N 30/60* (2006.01)
*G01N 30/02* (2006.01)

(52) U.S. Cl.
CPC ..... *G01N 30/6086* (2013.01); *G01N 30/6095* (2013.01); *G01N 2030/025* (2013.01); *G01N 2030/6056* (2013.01)

(58) Field of Classification Search
CPC .......... G01N 30/6086; G01N 30/6065; G01N 30/6095; G01N 2030/6056
See application file for complete search history.

(56) References Cited

U.S. PATENT DOCUMENTS

| | | | | |
|---|---|---|---|---|
| 2006/0243140 | A1* | 11/2006 | Lehmann | G01N 30/6086 96/101 |
| 2008/0092626 | A1* | 4/2008 | Lehmann | B01J 20/286 73/23.3 |

OTHER PUBLICATIONS

Syed Ali et al., MEMS-based semi-packed gas chromatography columns, Sensors and Actuators B, vol. 141, 2009, pp. 309-315.
Rekha S. Pai et al., Microfabricated Gas Chromatograph for Trace Analysis, 2008 IEEE International Conference on Technologies for Homeland Security, 2008, pp. 150-154.
(Continued)

*Primary Examiner* — Paul West (57) ABSTRACT

A wavy micro gas chromatography column includes a silicon substrate and a bonded glass cover. A micro channel having a rectangular cross section is etched on the silicon substrate and coated with a stationary phase film. A projection figure of the micro channel on the silicon substrate includes multiple regular wavy curves. Each wavy curve is formed through alternately connecting first upper arcs with first lower arcs. Because the groove has a curving structure, the carrier gas velocity is decreased as the increase of the arc angle, resulting in an improvement of the flow uniformity at the zones between two adjacent bends but also an enlarging nonsymmetric distribution at the bends. Thus, an optimal curving structure can make the overall flow more even, and in turn achieve a better separation performance compared to the straight channel columns. Meanwhile, a wavy channel realizes a longer column length on a given area.

4 Claims, 7 Drawing Sheets
(2 of 7 Drawing Sheet(s) Filed in Color)

(56) References Cited

OTHER PUBLICATIONS

Yi Li et al., Improvement of column efficiency in MEMS-Based gas chromatography column, RSC Advances, vol. 4, 2014, pp. 3742-3747.

Adarsh D. Radadia et al., New Column Designs for Microgc, Transducers & Eurosensors '07, 2007, pp. 2011-2014.

A.D. Radadia, The effect of microcolumn geometry on the performance of micro-gas chromatography columns for chip scale gas analyzers, Sensors and Actuators B, vol. 150, 2010, pp. 456-464.

Jianhai Sun et al., Fabrication and characterization of microelectromechanical systems-based gas chromatography column with embedded micro-posts for separation of environmental carcinogens, Journal of Chromatography A, vol. 1291, 2013, pp. 122-128.

Abhinav Bhushan et al., Fabrication of micro-gas chromatograph columns for fast chromatography, Microsyst Technol, 2007, vol. 13, pp. 361-368.

* cited by examiner

WAVY MICRO GAS CHROMATOGRAPHY COLUMN

CROSS REFERENCE OF RELATED APPLICATION

The application claims priority under 35 U.S.C. 119(a-d) to CN 201510577996.7, filed Sep. 11, 2015.

BACKGROUND OF THE PRESENT INVENTION

Field of Invention

The present invention relates to a technical field of gas chromatography, and more particularly to a wavy micro gas chromatography column.

Description of Related Arts

With the social development, the industrialization process, and the continuously rising living standard, the environmental pollution causes more and more problems. The emergency monitoring requires the environmental monitoring department to accurately identify the type, the concentration, the toxicity, and the distribution of the pollutant as quickly as possible. The portable gas chromatograph has the advantages of small volume, light weight, battery power supply and on-site operation. It can meet the requirements of different analysis environments and is generally able to qualitatively analyze the pollutant and obtain a preliminary quantitative result in minutes. Thus, developing a portable gas chromatograph having the high sensitivity, the high resolution, and the high cost performance has become an important research direction in the chromatography field.

Although the conventional gas chromatograph has the strong mixture separation ability, the conventional gas chromatograph has the problems of large volume, heavy weight, long separation time, and relatively high energy consumption. The micromachining technology is able to effectively realize the miniaturization of the gas chromatograph which accelerates the separation speed, consumes less power and becomes more portable.

Like the conventional chromatography column, the main performance index to examine the micro-electro-mechanical system (MEMS) chromatography column is the separation efficiency. Besides the factor of the stationary phase, the separation efficiency is also influenced by the geometric structure of the chromatography column. The main influence factors comprise following three points.

(1) The Aspect Ratio

Because the conventional MEMS chromatography columns are mostly micro-machined and etched through a deep reactive-ion etching (DRIE) technology, the cross section of the chromatography groove is rectangular, which is different from the circular cross section of the conventional capillary chromatography column. For the rectangular groove, the deeper the depth and the narrower the width, namely the larger the aspect ratio, the higher separation efficiency will be obtained for the MEMS chromatography column. The aspect ratio is the main influence factor of the separation efficiency.

(2) The Plane Layout of the Groove

Figure 1A:
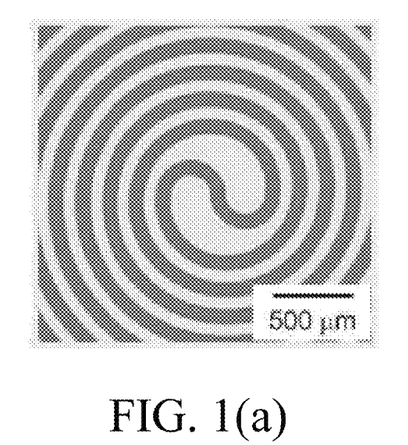
FIG. 1(a) is a photo of a conventional circular-spiral micro chromatography column.
Figure 1B:
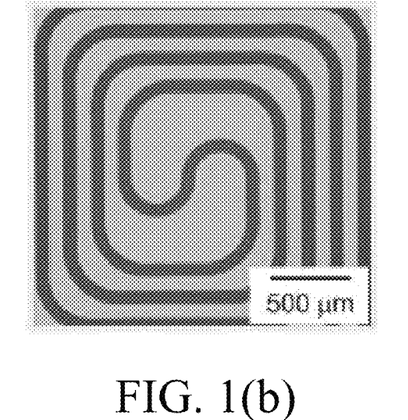
FIG. 1(b) is a photo of a conventional square-spiral micro chromatography column.
Figure 1C:
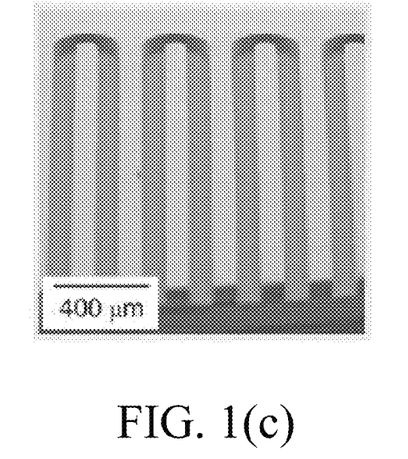
FIG. 1(c) is a photo of a conventional serpentine micro chromatography column.

The chromatography groove must have a certain length (generally 0.5-6 m). Thus, in order to coil the micro chromatography groove having the enough length on the silicon wafer which has an area as small as possible, the plane configurations of the conventional micro chromatography columns are mainly serpentine and spiral (as showed in FIG. 1). The University of Illinois, USA, systematically compared the separation performances of the circular-spiral, the square-spiral and the serpentine micro chromatography columns. The result demonstrated that, no matter under the isothermal mode or temperature-programmed mode, the serpentine chromatography column has the sharpest peak and the highest resolution, referring to the non-patent literature (Radadia A D, Salehi-Khojin A, Masel R I, et al. *The effect of microcolumn geometry on the performance of micro-gas chromatography columns for chip scale gas analyzers*, Sens Actuators B, 2010, 150: 456-464).

(3) The Microstructure in the Groove

Figure 2:
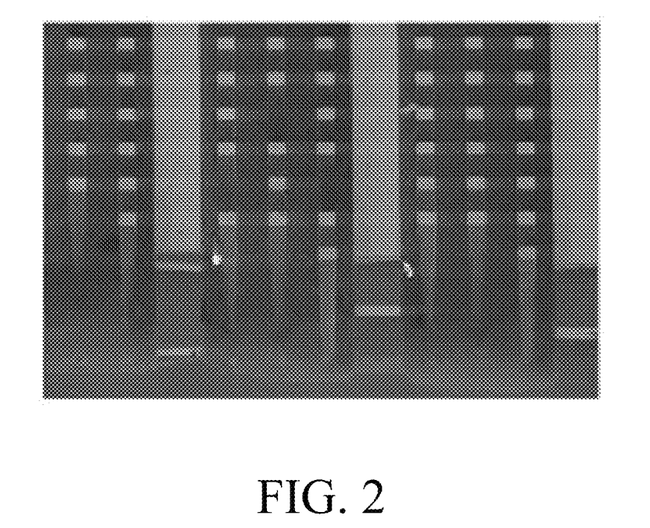
FIG. 2 is a photo of a conventional semi-packed micro chromatography column.

The above-described rectangular groove of the MEMS chromatography column is completely hollow and called open tubular column. When the rectangular groove has a microstructure having finer size (such as the micro posts showed in FIG. 2) micro-machined therein, the groove is called semi-packed column. Compared with the open tubular column having the same groove size, the semi-packed chromatography column has the higher separation efficiency, because the airflow in the semi-packed column is more uniform than in the open tubular column. The Virginia Polytechnic Institute and State University analyzed the airflow in the open tubular column and the semi-packed column by a finite element analysis software, and the result thereof is showed in FIG. 9 of the non-patent literature (Ali S, Ashraf-Khorassanib M, Taylor L T, et al. *MEMS-based semi-packed gas chromatography columns*, Sens Actuators B, 2009, 141: 309-315). The figure is a color drawing, wherein the carrier gas velocity in the red area is fastest and in the blue area is slowest. Thus, for the open tubular column, the airflow at the center is fastest and at the edge is slowest, leading to a laminated flow distribution for a deep vertical groove, which is disadvantageous for the contact between the gas molecules and the stationary phase. In comparison, the laminar flow effect of the gas in the semi-packed column is weakened, which increases the separation efficiency of the chromatography column. Thus, the flow distribution in the groove of the micro chromatography column has a great effect on the separation performance of the chromatography column.

Although the semi-packed column has the higher separation efficiency than the open tubular column, the MEMS machining of the semi-packed column is more difficult since the much smaller size and finer substructures are needed to be realized.

SUMMARY OF THE PRESENT INVENTION

An object of the present invention is to provide a wavy micro gas chromatography column, so as to solve problems mentioned above in prior arts.

The present invention adopts a technical idea of decreasing the laminar flow effect and thus increasing the flow field uniformity through bending the channel to a wavy configuration instead of embedding micro posts in the channel. A plane structure of a micro chromatography groove is based on a serpentine groove structure, but every straight section of a serpentine groove is replaced by a wavy channel section, in such a manner that the flow velocity is relatively decreased and thus the laminar flow effect is decreased, which increases the contact and interaction between gas molecules and the stationary phase, and finally obtains a higher separation efficiency.

Technical solutions of the present invention are described as follows.

A wavy micro gas chromatography column comprises a silicon substrate and a glass cover bonded to the silicon substrate. A groove, having a rectangular cross section, is etched on the silicon substrate. After being covered by the glass cover, the groove is sealed and a micro channel is formed. Four inner walls of the micro channel are coated by a stationary phase film. The micro channel comprises multiple wavy channel sections. A projection figure of the micro channel on the silicon substrate is formed by multiple regular wavy curves, and each wavy curve is formed through alternately connecting first upper arcs with first lower arcs.

Preferably, for every first upper and lower arc, a corresponding arc angle is in a range of 120°-150°, and a corresponding curvature radius is 20%-50% of a width W of the micro channel.

Preferably, for every first upper and lower arc, the corresponding arc angle is 136° and the corresponding curvature radius is 14.3 µm; and, the width of the micro channel is 40 µm.

Preferably, every two adjacent wavy channel sections are connected by a second arc having an arc angle of 180°.

Preferably, an air inlet and an air outlet of the micro channel are arranged at a side of the silicon substrate, and, after cutting the silicon substrate from a silicon wafer, an opening at the side is formed.

The present invention has following beneficial effects. Through simulating and analyzing with a finite element software, relatively to a straight groove, the carrier gas velocity of a wavy groove is decreased because of a curving structure of the wavy groove, which increases the interaction between the gas molecules and the stationary phase, thus helps to obtain a higher separation efficiency. Through choosing a suitable first arc, the enhanced contact between the gas molecules and the stationary phase is guaranteed without seriously prolonging the analysis time. Meanwhile, compared with the straight groove, the wavy groove realizes a longer column length on a given area, thus the surface area of the stationary phase is relatively increased, which accordingly increases the gas distribution coefficient and the column efficiency.

These and other objectives, features, and advantages of the present invention will become apparent from the following detailed description, the accompanying drawings, and the appended claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the figures: 1-silicon substrate; 2-glass cover; 3-groove; 4-stationary phase film; 5-air inlet; and 6-air outlet.

DETAILED DESCRIPTION OF THE PREFERRED EMBODIMENT

The present invention is further illustrated with a preferred embodiment. One skilled in the art will easily know the advantages and the benefits of the present invention from the preferred embodiment and understand that the embodiment of the present invention as shown in the drawings and described below is exemplary only and not intended to be limiting.

Figure 3:
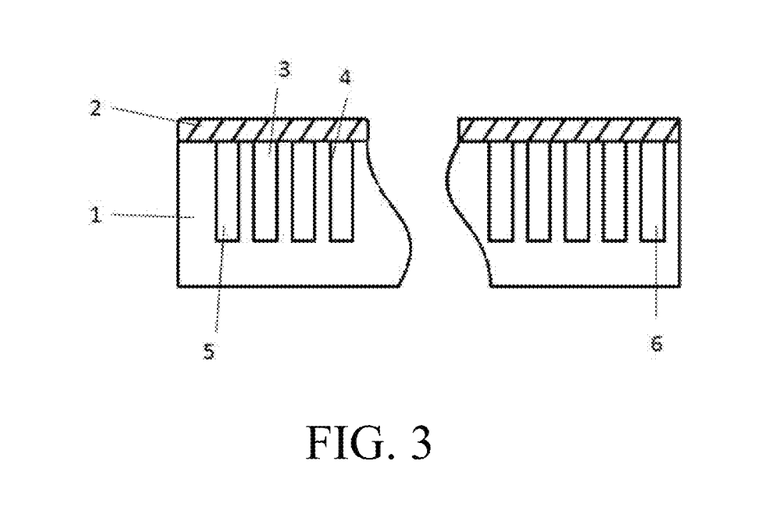
FIG. 3 is a cross sectional view of a wavy micro gas chromatography column according to a preferred embodiment of the present invention.

According to a preferred embodiment of the present invention, a wavy micro gas chromatography column comprises a silicon substrate 1 and a glass cover 2 (7740 glass) bonded to the silicon substrate 1. A groove 3, having a rectangular cross section, is etched on the silicon substrate 1. After being covered by the glass cover 2, the groove 3 is sealed and a micro channel is formed. Four inner walls of the micro channel are coated by a stationary phase film 4. A cross sectional view of the wavy micro gas chromatography column is showed in FIG. 3. The micro channel comprises multiple wavy channel sections. A projection figure of the micro channel on the silicon substrate 1 comprises multiple regular wavy curves.

Figure 4:
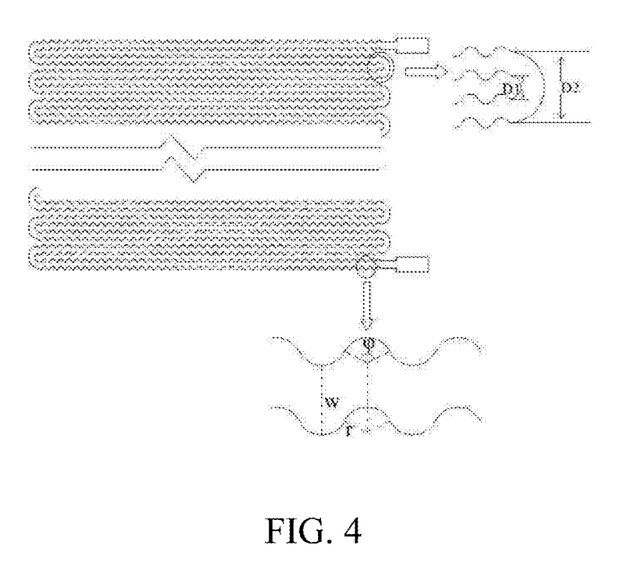
FIG. 4 is a plane sketch view of the wavy micro gas chromatography column according to the preferred embodiment of the present invention.

Each wavy curve is formed through alternately connecting first upper arcs with first lower arcs. Every first upper and lower arc has a radius, r, and an arc angle, φ. A width of the micro channel is W. A top view of the wavy micro gas chromatography column is showed in FIG. 4. For every first upper and lower arc, the corresponding arc angle is in a range of 120°-150° and the corresponding curvature radius is 20%-50% of the width W of the micro channel. Every two adjacent wavy channel sections are connected by a second arc having an arc angle of 180°. Every second arc is larger than the first arcs. An air inlet 5 and an air outlet 6 of the micro channel are arranged at a side of the silicon substrate 1, and, after cutting the silicon substrate 1 from a silicon wafer, an opening at the side is formed.

The key point for the layout design is the curving degree of the multiple wavy channel sections, which is determined by the arc angle φ of the first upper and lower arcs, and the proportional relationship between the curvature radius r of the first upper and lower arcs and the width W of the micro channel. Four different micro channels having a same width of 40 μm are processed with a finite element simulation, and four flow field simulation results thereof are showed in FIG. 5(a)-FIG. 5(d). Among them, FIG. 5(a) refers to a straight long section in a serpentine channel, while FIG. 5(b), FIG. 5(c), and FIG. 5(d) correspond to wavy channel sections with arc angles of 90°, 136°, and 180° and curvature radiuses of 18.5 μm, 14.3 μm, and 13.3 μm, respectively.

Figure 5A:
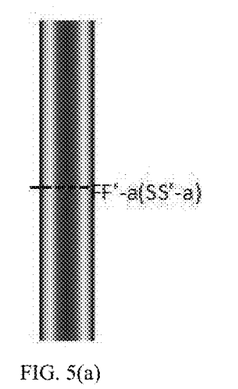
FIG. 5(a) is a velocity contour plot of the serpentine column.

It can be seen from FIG. 5(a) that the flow distribution for a straight long segment along the channel (longitudinally distributed) is uniform but accompanying a large velocity difference across the channel (laterally distributed), thus suffering a strong laminar flow effect. When the straight section is folded to form a wavy channel section, the longitudinal distribution is no more uniform, causing a slowest velocity at bends and a fastest velocity at the middle of two neighboring bends. Lateral distributions across the two sides are extracted because of directly relating to peak broadening and being more important for a gas chromatography column whereas the longitudinal distribution is mainly contribute to the separation time and less important. It is clear that each velocity profile at a FF' section possesses a Gaussian distribution with a good symmetry as showed in FIG. 5(f). It can be seen from FIG. 5(f) that the flow velocity decreases in FF'-a, FF'-b, FF'-c, and FF'-d sequences, leading to the lateral distribution become more and more uniform in the same order, which is beneficial to decrease the laminar flow effect. However, velocity profiles at the SS' sections must also be taken into consideration as a whole. As showed in FIG. 5(g), distribution curves are not Gaussian-typed, wherein the flow velocity is faster at an inner side and slower at an outside side. More importantly, the nonsymmetry increases in SS'-a, SS'-b, SS'-c, and SS'-d sequences, indicating that a design with a large arc angle, as showed in FIG. 5(d), is not optimal for increasing the separation efficiency. Moreover, the design showed in FIG. 5(d) has another shortcoming that the average flow velocity is too slow, which will seriously prolong the elude time.

Figure 5B:
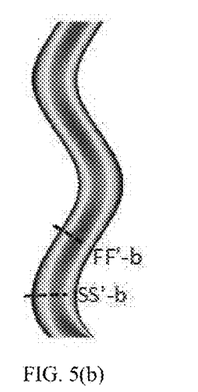
FIG. 5(b) is a velocity contour plot of a wavy column with an arc angle of 90°.
Figure 5C:
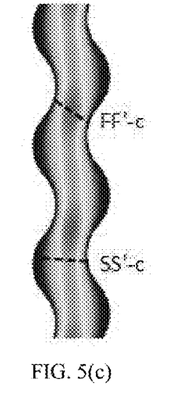
FIG. 5(c) is a velocity contour plot of a wavy column with an arc angle of 136°.
Figure 5D:
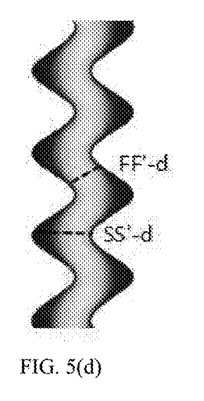
FIG. 5(d) is a velocity contour plot of a wavy column with an arc angle of 180°.

On the other hand, a design with a small arc angle is not optimal as well, since the differences of the flow distribution between a design showed in FIG. 5(b) and a design showed in FIG. 5(a) are not remarkable, thus the design showed in FIG. 5(b) fails to obtain a large gas chromatography efficiency improvement. A design showed in FIG. 5(c) effectively decreases the average flow velocity to a suitable range, resulting in a remarkable improvement on the flow uniformity at the FF' section and a slight and acceptable nonsymmetry at the SS' section. Therefore, the design showed in FIG. 5(c) is an optimal layout configuration for a wavy column. According to simulations, the most critical factors for the wavy column are the arc angle which is preferably from 120° to 150° and the curvature radius which is roughly in a range of 20%-50% of the channel width.

The non-patent literature (Bhushan A, Yemane D, Trudell D, et al, *Fabrication of micro-gas chromatograph columns for fast chromatography*, Microsyst. Technol. 2007, 13: 361-368) reported a zigzag micro chromatography column. A flow field distribution of the zigzag micro chromatography column is simulated, wherein the width of the channel of the zigzag micro chromatography column is 40 μm, each straight section of the channel has a length of 54.3 μm, and every two adjacent straight sections have a 90° bend.

Figure 5E:
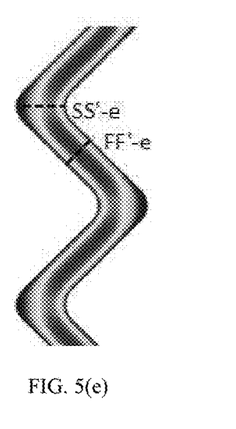
FIG. 5(e) is a velocity contour plot of a zigzag column.
Figure 5F:
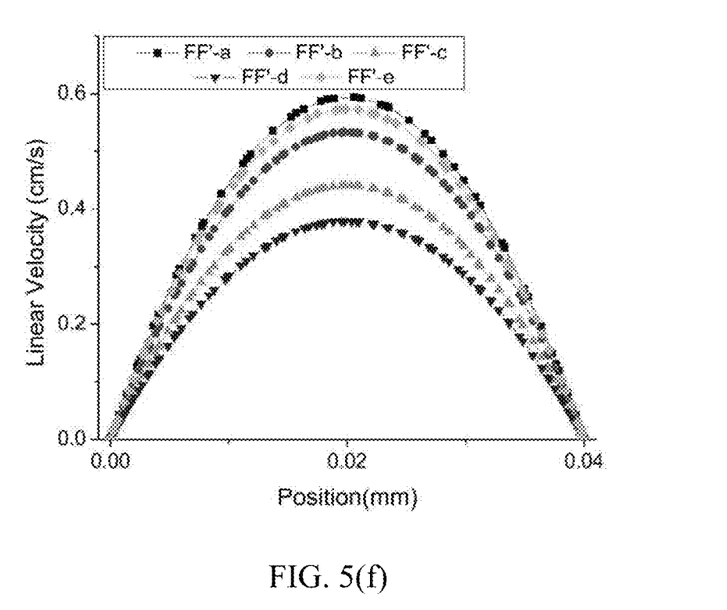
FIG. 5(f) is a sketch view of velocity profiles of the serpentine column, the wavy column with the arc angle of 90°, the wavy column with the arc angle of 136°, the wavy column with the arc angle of 180°, and the zigzag column at a FF' section.
Figure 5G:
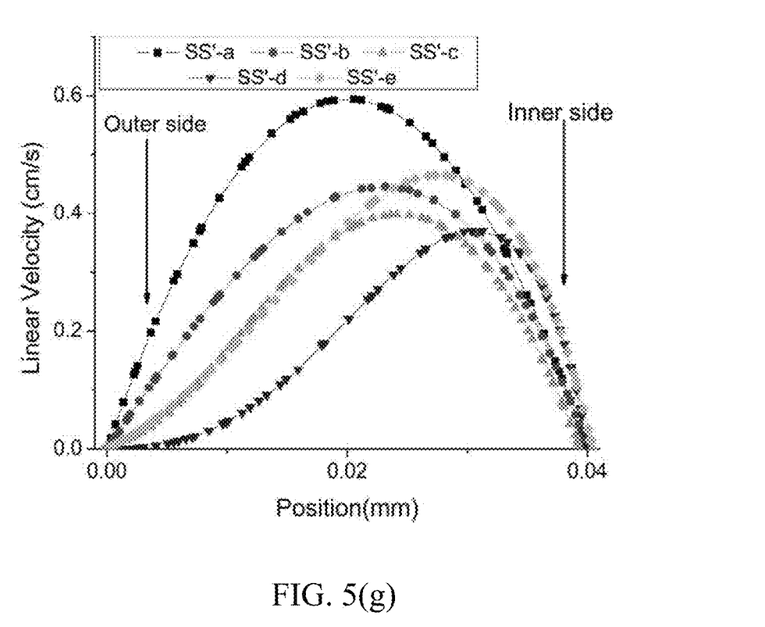
FIG. 5(g) is a sketch view of velocity profiles of the serpentine column, the wavy column with the arc angle of 90°, the wavy column with the arc angle of 136°, the wavy column with the arc angle of 180°, and the zigzag column at a SS' section.

A velocity contour plot of the zigzag column is showed in FIG. 5(e) and velocity profiles thereof at the FF', SS' sections are plotted in FIG. 5(f) and FIG. 5(g) as well. It can be seen from FIG. 5(f) and FIG. 5(g) that flow distributions of the zigzag column are worse than the flow distributions of the wavy column showed in FIG. 5(b), let alone the wavy column showed in FIG. 5(c). Furthermore, the velocity profile at the SS' section of the zigzag column shows the strongest nonsymmetry though the 90° bends are smoothed. The nonsymmetry greatly increases the peak broadening and causes the zigzag column to be even worse than the serpentine column, as demonstrated by the zigzag column separation experiments.

Compared with the serpentine column, another advantage of the wavy column is the extended column length. When the two columns have the same groove width and the same groove interval, the relationship between the total length of the wavy column ($L_w$) and the total length of the serpentine column ($L_s$) on a silicon substrate having the same area can be roughly expressed by the following equation:

$$L_w = \frac{\varphi \cdot 2\pi r}{360 \cdot 2r\sin\varphi/2} \cdot L_s = \frac{\varphi \cdot \pi}{360 \cdot \sin\varphi/2} \cdot L_s, \tag{1}$$

wherein the arc angle φ is in degree. It can be seen that the total length increasement is only related to the arc angle. For the arc angles of 90°, 136° and 180°, the wavy columns are 11%, 28% and 57% longer than the corresponding serpentine column, respectively. An increase of the column length is beneficial to obtain a higher separation efficiency.

Based on the above simulation results, the wavy micro chromatography column showed in FIG. 5(c) is selected as the optimal one and fabricated by the micro-electro-mechanical system (MEMS) technology.

A preparation method of the wavy micro chromatography column provided by the present invention comprises following steps.

1) Photomask Designing

The total length of the micro chromatography column is designed as 2 m, and the width W of the groove is 40 μm. Each wavy curve is formed through alternately connecting the first upper arcs with the first lower arcs. Every first upper and lower arc has the radius r of 14.3 μm and the arc angle φ of 136°. Every two adjacent wavy channel sections are connected by the second arc having the arc angle φ of 180°. Every second arc has an inner diameter D1 of 40 μm and an outer diameter D2 of 120 μm. The interval between two neighbouring wave channel sections is also 40 μm.

2) Mask Preparing

A monocrystalline silicon wafer having a thickness of 500 μm is adopted as the substrate; and an aluminum film having a thickness of about 100 nm as a hard mask is deposited on the monocrystalline silicon wafer by electron beam evaporation.

3) Photolithography

A photoresist AZ6112 is spin-coated on the wafer; the pattern on the photomask is transferred to the photoresist through exposing and developing; and the aluminum film is etched by reactive-ion etching (RIE), so as to further transfer the pattern of the photoresist to the aluminum film.

4) DRIE

An etching gas of $SF_6$ and a protection gas of $C_4F_8$ are alternatively introduced into the etching chamber, so as to etch the silicon wafer to a depth of 300 μm.

5) Silicon-Glass Bonding

Pyrex7740 glass is anodically bonded on the top of the silicon wafer, so as to seal the groove of the chromatography column.

6) Cutting

At a preset position, the wafer is cut, so as to expose the gas inlet/outlet of the micro chromatography column at the side of the silicon substrate.

7) Stationary Phase Coating

A mixture of 5% diphenyl, 1% vinyl, and 94% polydimethylsiloxane (SE-54) is coated at the inner wall of the groove by static coating procedure to serve as the stationary phase film.

In the above fabrication steps, the key step is the design of the wavy chromatography column. The subsequent MEMS machining steps of the present invention are similar as the other micro chromatography columns, which is able to be finished through matured MEMS technology. According to the preferred embodiment of the present invention, the aspect ratio is 7.5, and the minimum line width is 40 μm, so that MEMS machining is not difficult.

Figure 6:
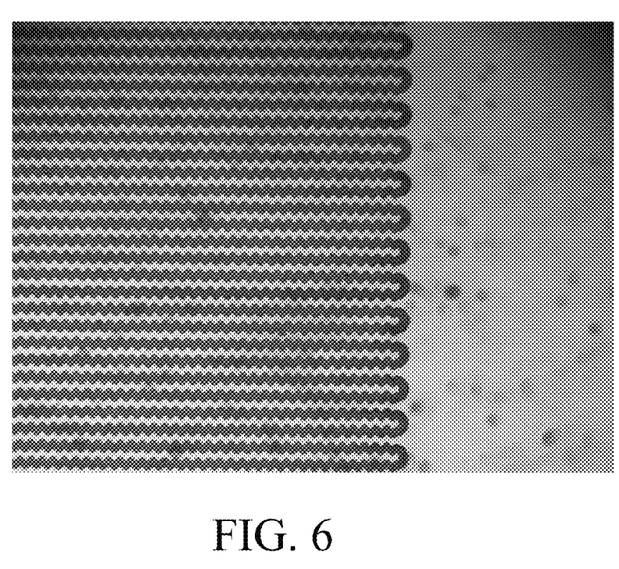
FIG. 6 is a photo of the wavy micro gas chromatography column (local view) according to the preferred embodiment of the present invention.

An optic photo of the finished wavy micro gas chromatography column (local view) is showed in FIG. 6.

Figure 7A:
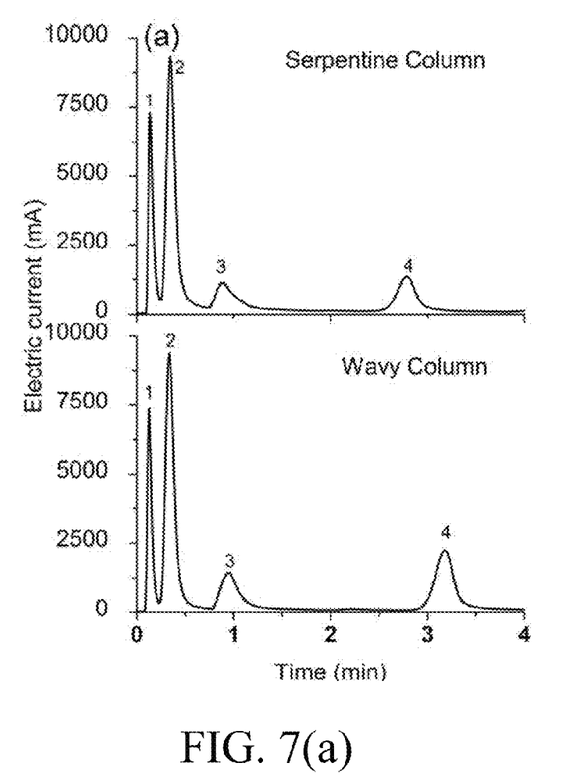
FIG. 7(a) is chromatograms of the wavy micro gas chromatography column and the serpentine chromatography column.
Figure 7B:
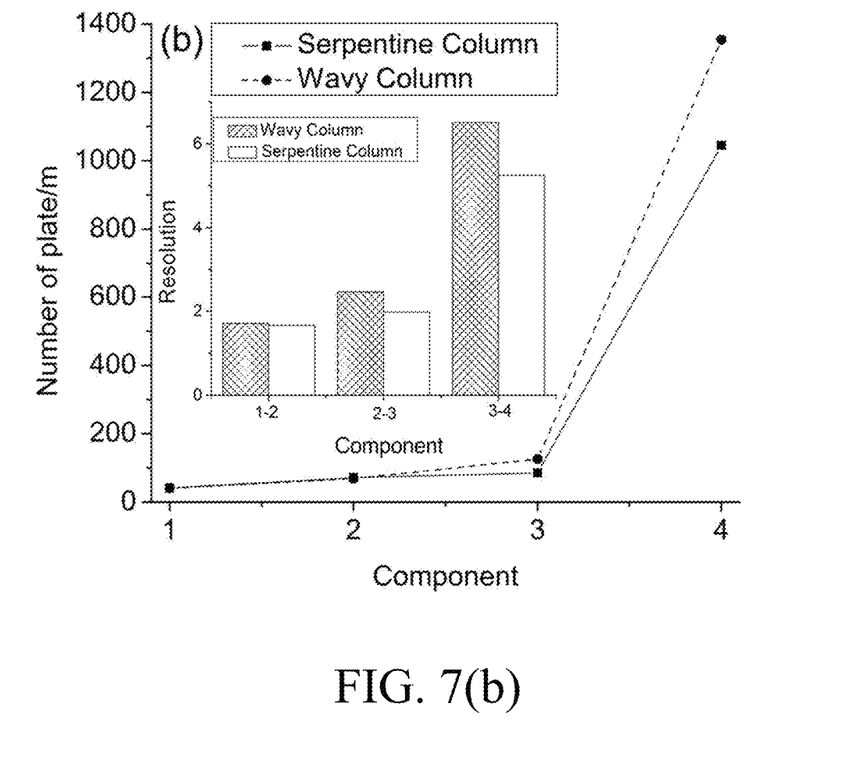
FIG. 7(b) is a comparison diagram of plate number and column resolution of the wavy micro gas chromatography column and the serpentine chromatography column.

Separation result of the wavy chromatography column on a mixture having four components is showed in FIG. 7, wherein the four components are respectively dichloroethane, methylbenzene, dimethyl methyl phosphonate, and methyl salicylate. For comparison, separation result of the serpentine chromatography column having the same characteritics (200 cm long, 40 μm wide, 300 μm deep, and a SE-54 stationary phase) is also given. Chromatograms of the wavy chromatography column and the serpentine chromatography column are showed in FIG. 7(a). It can be seen from FIG. 7(a) that the wavy chromatography column has a slightly longer separation time than the serpentine chromatography column. However, the most important parameters to characterize the performance of a chromatography column are column resolution and plate number. It can be seen from FIG. 7(b) that the peak to peak resolution of the wavy column is in the range of 1.8 to 6.5, demonstrating a complete separation of two neighbouring components. Compared with the serpentine column, the improvement of the wavy column in resolution is as high as 20%. As for the plate number, the wavy column possesses equal or higher values, indicating a higher separation efficiency. Thus, the wavy chromatography column has a better separation performance than the serpentine chromatography column.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A wavy micro gas chromatography column, comprising: a silicon substrate and a glass cover bonded to said silicon substrate; wherein a groove, having a rectangular cross section, is etched on said silicon substrate; after being covered by said glass cover, said groove is sealed and a micro channel is formed; four inner walls of said micro channel are coated by a stationary phase film; said micro channel comprises multiple wavy channel sections; a projection figure of said micro channel on said silicon substrate is formed by multiple regular wavy curves; each wavy curve is formed through alternately connecting first upper arcs with first lower arcs; a corresponding arc angle of every first upper and lower arc is in a range of 120°-150°, and a corresponding curvature radius is 20%-50% of a width W of said micro channel.

2. The wavy micro gas chromatography column, as recited in claim 1, wherein said corresponding arc angle of every first upper and lower arc is 136° and said corresponding curvature radius is 14.3 μm; and, said width of said micro channel is 40 μm.

3. The wavy micro gas chromatography column, as recited in claim 1, wherein every two adjacent wavy channel sections are connected by a second arc having an arc angle of 180°.

4. The wavy micro gas chromatography column, as recited in claim 1, wherein an air inlet and an air outlet of said micro channel are arranged at a side of said silicon substrate; and, after cutting said silicon substrate from a silicon wafer, an opening at the side is formed.

* * * * *